United States Patent [19]

Phuc

[11] Patent Number: 4,702,678
[45] Date of Patent: Oct. 27, 1987

[54] OSCILLATOR FOR VENTILATION APPARATUS FOR ARTIFICIAL RESPIRATOR

[75] Inventor: Tran N. Phuc, Ohmiya, Japan

[73] Assignee: Senko Medical Instrument Mfg. Co. Ltd., Tokyo, Japan

[21] Appl. No.: 866,225

[22] Filed: May 22, 1986

[30] Foreign Application Priority Data

May 29, 1985 [JP] Japan ................ 60-80621[U]

[51] Int. Cl.[4] ............................................. F04B 17/00
[52] U.S. Cl. ..................................... 417/360; 403/364
[58] Field of Search ............... 417/238, 360, 454, 572; 403/309, 313, 360, 364; 248/672, 674, 676

[56] References Cited

U.S. PATENT DOCUMENTS

| | | | |
|---|---|---|---|
| 718,306 | 1/1903 | Boring | 403/360 X |
| 1,672,205 | 6/1928 | Eisler | 418/13 |
| 2,739,537 | 3/1956 | Sadler et al. | 417/360 |
| 3,447,479 | 6/1969 | Rosenberg | 417/360 X |
| 3,697,197 | 10/1972 | Berglund et al. | 417/360 |
| 4,204,815 | 5/1980 | Le Blanc | 418/96 X |

Primary Examiner—Leonard E. Smith
Attorney, Agent, or Firm—Hoffmann, Dilworth, Barrese & Baron

[57] ABSTRACT

An oscillator for imparting oscillation at a high frequency to respiratory gas in a pneumatic circuit of a high frequency oscillatory ventilation apparatus for artificial respiration includes a cylinder unit mounted on a base plate and including a cylinder, a piston rod slidably extending through the cylinder along an axis thereof, and a piston fixedly mounted on the piston rod and received in the cylinder for sliding movement therealong for applying oscillation to the pneumatic circuit. A first engaging member, mounted on a reciprocable output shaft of a motor mounted on the base plate, engages a second engaging member mounted on the piston rod to connect the output shaft to the piston rod to reciprocally move the piston, the engagement being made in a manner to allow the second engaging member to move out of engagement with the first engaging member in a direction perpendicular to an axis of the piston rod. A third engaging member on the base plate engages a fourth engaging member on the cylinder in a manner to allow the fourth engaging member to move out of engagement therewith in said direction. A fastening member releasably holds the fourth engaging member against movement relative to the third engaging member, thereby holding the cylinder unit against movement relative to the base plate and the motor.

5 Claims, 3 Drawing Figures

OSCILLATOR FOR VENTILATION APPARATUS FOR ARTIFICIAL RESPIRATOR

BACKGROUND OF THE INVENTION

1. Field of the Invention

This invention relates generally to a high frequency oscillatory ventilation apparatus for artificial respiration and particularly to an oscillator for use in such ventilation apparatus.

2. Related Art

Japanese Utility Model Application No. 59-17747 discloses a high frequency oscillatory ventilation apparatus for artificial respiration shown in FIG. 1. This ventilation apparatus comprises a pneumatic circuit including a patient circuit 10 including an inspiration tube 12a and three tubes 12b, 12c and 12d, these four tubes being connected together at a junction point to communicate with one another. An oscillator 14 comprises a cylinder unit including a cylinder 14a and a piston 14b received in the cylinder 14a, and a motor 16 connected to the piston 14b through a crank 18 and a connecting rod 20, so that the piston 14b is reciprocably moved along the cylinder 14a. The tube 12b is connected to the oscillator 14, so that the oscillator 14 imparts oscillation normally at a high frequency of not less than 4 Hz to respiratory gas in the patient circuit 10, thereby promoting the diffusion of the gas in the respiratory tract of the patient to effect artificial respiration. The tube 12d is connected to a moistening/gas feed tube 22 to feed respiratory gas from a gas source 24 to the patient circuit 10, and a respiratory pressure-detecting line 26 is connected to the tube 12b. A positive-pressure generating unit 28 comprises a cylindrical member 28a and a nozzle 28b having a discharge end received loosely in an open end of the cylindrical member 28a. The respiratory gas is fed from the gas source 24 to a gas feed conduit 30 via any one of the following three feed paths:

(1) the first path constituted by a conduit 31 connected to the outlet side of a solenoid valve 32, a regulator 33 and a check valve 34.

(2) the second path constituted by the conduit 31, a regulator 35, a check valve 36 and a solenoid valve 37.

(3) the third path constituted by the conduit 31 and the solenoid valve 37. The solenoid valve 32 is controlled by a controller 38 including a microprocessor to selectively feed the respiratory gas from the gas source 24 to the conduit 31. The solenoid valve 37 has two inlets 37a and 37b and one outlet 37c, and under the control of the controller 38, the solenoid 37 has three modes of operation. More specifically, in a first mode, the first inlet 37a communicates with the outlet 37c, and in a second mode, the inlet 37b communicates with the outlet 37c, and in a third mode, the solenoid 37 is closed. Pressure gauges 39 and 40 monitor the output pressures of the regulators 33 and 35, respectively. The output pressures of the regulators 33 and 35 are set at different predetermined levels, respectively. With this arrangement, the pressure of the respiratory gas fed to the nozzle 28b can be changed by selecting any one of the above three feed paths, so that the pressure in the cylindrical member 14a is always kept at pressure P1 lower than the pressure P2 of the respiratory gas in the patient circuit 10.

A branch conduit 41 is connected between the oscillator 14 and the patient circuit 10. A plug 42 is mounted on the open end of the branch conduit 41 through which it communicates with the atmosphere, and the plug 42 is actuated by a solenoid 43 to selectively open and close the open end of the branch conduit 41. The solenoid 43 is operated under the control of the controller 38 in accordance with a detected value of a pressure sensor 44, so that the pressure P2 in the patient circuit 10 is always kept higher than the pressure P1 in the positive pressure-generating unit 28. With this arrangement, the breathing gas and the respiration gas from the gas source 24 can be smoothly discharged from the ventilation apparatus via the positive pressure-generating unit 28.

A protective circuit 45 is connected between the solenoid valve 32 and the pressure sensor 44 for preventing moisture from intruding from the patient circuit 10 into the pressure sensor 44 through the pressure detecting line 26. The protective circuit 45 comprises a gas regulator 46, a pressure switch 47, a resistor 48. When the respiratory gas does not flow properly from the regulator 46 to the pressure sensor 44, the pressure switch 47 is activated to feed an alarm signal to the controller 38.

Those portions of the above ventilation through which the expired gas from the patient pass, such as the patient circuit 10, the conduits adjacent thereto and the interior of the cylinder unit of the oscillator 14, must be cleaned and sterilized for the next use. Heretofore, the patient circuit and the conduits adjacent thereto, once used, have been discarded since they are relatively inexpensive. However, the cylinder unit could not be disposed of once it is used because it is relatively expensive. Therefore, each time the cylinder unit is used, it is cleaned and sterilized. The cylinder unit of the oscillator 14 is coupled to the motor 16 and also fixed to a base plate, though removably. Therefore, each time the cleaning and sterilization are effected, the coupling between the cylinder unit and the motor must be released, and the cylinder unit must be removed from the base plate. In addition, the motor must be detached from the base plate. Thus, the maintenance of the ventilation apparatus is rather cumbersome.

SUMMARY OF THE INVENTION

It is therefore an object of this invention to provide an oscillator for a high frequency oscillatory ventilation apparatus for artificial respiration in which a cylinder unit can be easily releasably mounted on a base plate and in which the cylinder unit can be easily releasably connected to the motor.

According to the present invention, there is provided an oscillator for imparting oscillation at a high frequency to respiratory gas in a pneumatic circuit of a high frequency oscillatory ventilation apparatus for artificial respiration, said oscillator comprising:

(a) an elongated base plate;

(b) a motor mounted on said base plate and having an output shaft for reciprocal movement along an axis thereof;

(c) a cylinder unit comprising a cylinder adapted to be connected to the pneumatic circuit, a piston rod slidably extending through said cylinder along an axis thereof, and a piston fixedly mounted on said piston rod and received in said cylinder for sliding movement therealong for applying oscillation to the pneumatic circuit;

(d) a first engaging means mounted on said output shaft of said motor;

(e) a second engaging means mounted on said piston rod, said first engaging means engaging said second engaging means to connect said output shaft to said piston rod to reciprocally move said piston, said first engaging means engaging said second engaging means in a manner to allow said second engaging means to move out of engagement therewith in a direction perpendicular to an axis of said piston rod;

(f) a third engaging means on said base plate, there being provided a fourth engaging means on said cylinder, said third engaging means engaging said fourth engaging means in a manner to allow said fourth engaging means to move out of engagement therewith in said direction; and (g) fastening means for releasably holding said fourth engaging means against movement relative to said third engaging means, thereby holding said cylinder unit against movement relative to said base plate and said motor.

DESCRIPTION OF THE PREFERRED EMBODIMENT OF THE INVENTION

Figure 1:
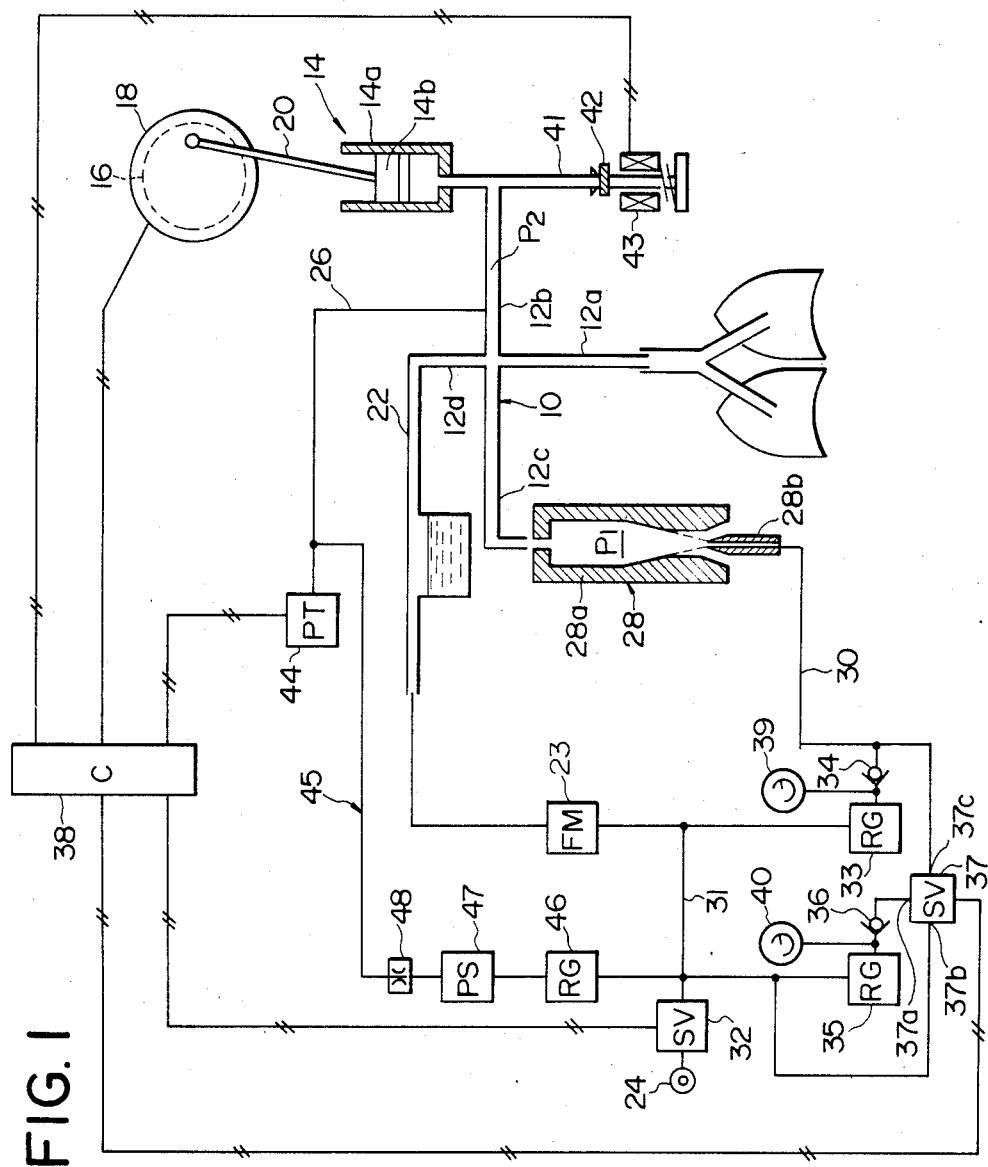
FIG. 1 is a block diagram of a high frequency ventilation apparatus for artificial respiration.
Figure 2:
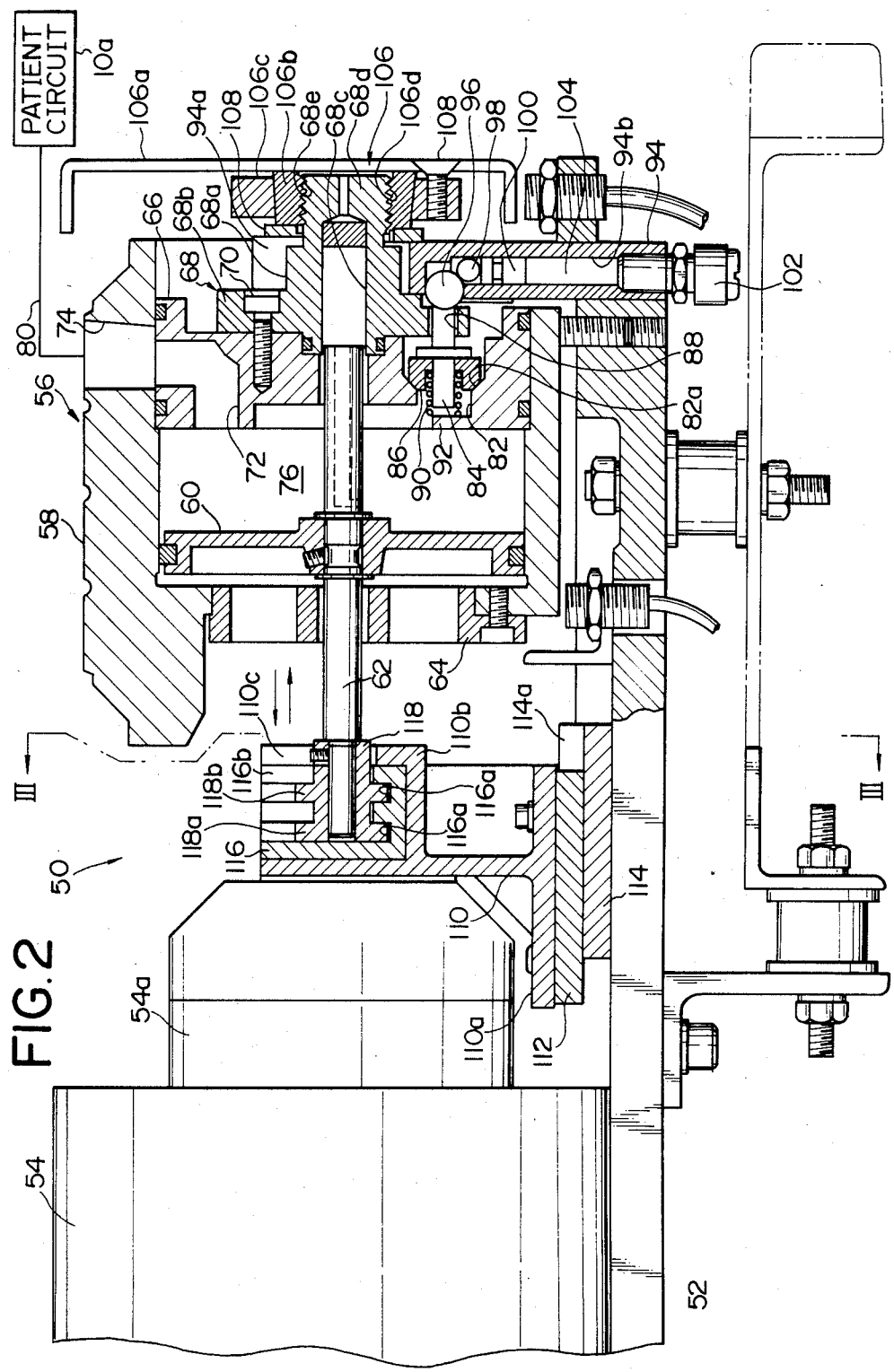
FIG. 2 is a partly cross-sectional, side elevational view of an oscillator, provided in accordance with the invention, for use in the ventilation apparatus of FIG. 1.
Figure 3:
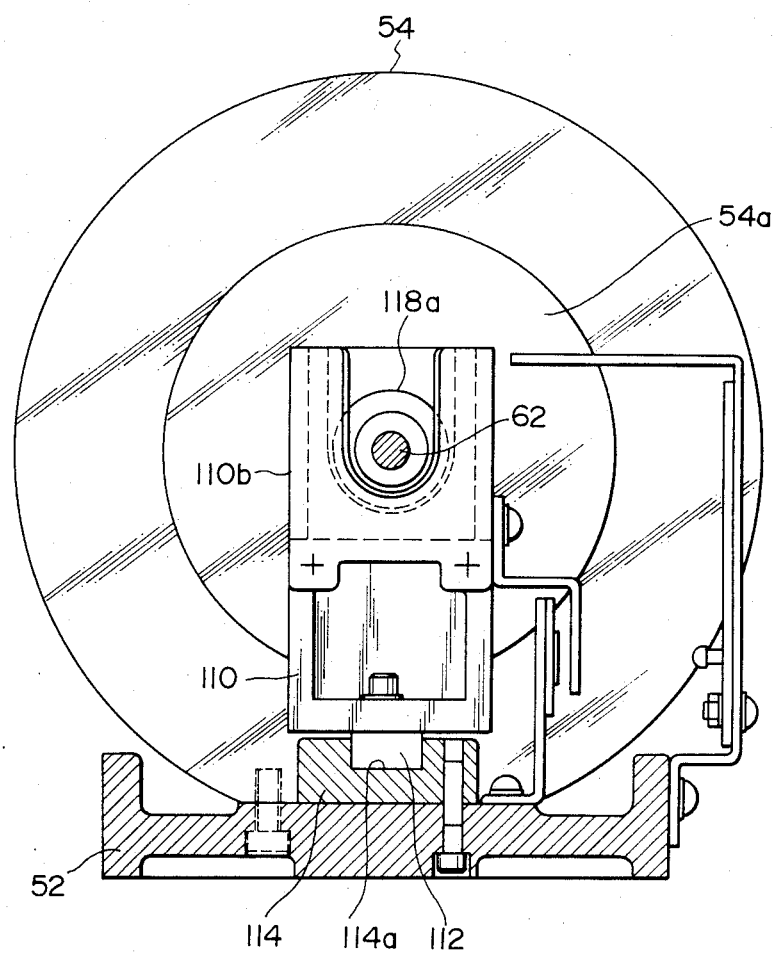
FIG. 3 is an view taken along the line III—III of FIG. 1.

FIG. 2 shows an oscillator 50 for imparting oscillation normally at a high frequency of not less than 4 Hz to respiratory gas in a patient circuit 10a of a high frequency oscillatory ventilation apparatus for artificial respiration. The oscillator 50 comprises an elongated base plate 52, a motor 54 and a cylinder unit 56 including a cylinder 58, a piston 60 received in the cylinder 58, and a piston rod 62 on which the piston 60 is fixedly mounted. A reciprocable output shaft 54a of the motor 54 is connected to the piston rod 62 as later described. The cylinder 58 includes a pair of first and second end plates 64 and 66 fixedly secured to the opposite end portions thereof. The piston rod 62 slidably extends through the end plates 64 and 66, and the piston 60 is disposed between the end plates 64 and 66. The cylinder 58 also includes an end member 68 which includes a generally cylindrical body 68a and a peripheral flange 68b formed around the body 68a, and is fixedly secured to the outer face of the second end plate 66 by screws 70 passing through the flange 68b into the second end plate 66. The cylindrical body 68a having an axial bore 68c opening to one end face facing the first end plate 64. The distal end of the piston rod 62 is slidably received in the bore 68c of the end member 68.

A passageway 72 is formed in the second end plate 66 and opens at opposite ends to the inner face thereof and the outer peripheral surface thereof, respectively. A passageway 74 is also formed through the peripheral wall of the cylinder 58, and communicates with the passageway 72, so that a cylinder chamber 76, defined by the cylinder 58, the piston 60 and the second end plate 66, communicates to the patient circuit 10a through a conduit 80. A port 82 is formed through the second end plate 66 and disposed in generally diametrically opposite relation to the passageway 72. A tapered valve seat 82a is formed on a peripheral surface defining the port 82, and a rod 84 is received in the port 82 and carries a valve member 86. The rod 84 extends slidably extends through an aperture 88 formed through the flange 68b of the end member 68. A compression coil spring 90 is wound around the rod 84 and acts between the valve member 86 and a radially-extending portion 92 formed on the second end plate 66 adjacent to the port 82 to urge the valve member 86 toward the end member 68.

An elongated connecting plate 94 is fixedly secured to one end of the base plate 52 remote from the motor 54, and is disposed perpendicular to the base plate 52. The connecting plate 94 has an opening or notch 94a formed therein and opening to an upper end thereof. The cylindrical body 68a of the end member 68 is fitted in the opening 94a for sliding movement upwardly in a direction perpendicular to the axis of the piston rod 62, with the inner surface of the connecting plate 94 held against the outer surface of the flange 68b of the end member 68. The connecting plate 94 has an internal bore 94b opening at one end to the lower end of the plate 94, the bore 94b also opening to the inner surface of the plate 94 at an upper end thereof. A steel ball 96 is movably received in the upper end of the bore 94b and is held against the outer end of the rod 84 remote from the valve member 86. A movable smaller steel ball 98 and a slidable seal plug 100 are also received in the bore 94b. A seal plug 102 is sealingly fitted in the lower end of the bore 94b. Gas under pressure is filled in a space 104 in the bore 94b between the plugs 100 and 102. The pressure in the gas-filled space 104 is greater than the pressure or force applied by the coil spring 90, so that the valve member 86 is normally held in sealing engagement with the valve seat 82a. When the pressure in the cylinder chamber 76 exceeds a predetermined pressure which is equal to the pressure in the bore 94b in which the pressurized gas is filled, the valve member 86 is moved out of sealing engagement with the valve seat 82a together with the rod 84 against the pressure in the bore 94b thereby communicating the cylinder chamber 76 with ambient atmosphere The cylinder unit 56 is fixed with respect to the base plate 52 through a fastening member 106. More specifically, the fastening member 106 comprises an elongated base portion 106a, an annular portion 106b disposed one side of the base portion 106, and a ring portion 106c fitted around the annular portion 106b and fixedly secured thereto. The ring portion 106c is fixed to the base portion 106a by screws 108, and hence the annular portion 106b is also fixed with respect to the base portion 106a.

The cylindrical body 68a has a reduced diameter portion 68d at one end portion thereof remote from the flange 68b, and the reduced diameter portion 68d has external threads 68e around the outer peripheral surface thereof. A washer 108 is mounted on the reduced diameter portion 68b. The annular portion 106b has internal threads 106d formed on the inner peripheral surface thereof. The annular portion 106b of the fastening member 106 is threaded on the reduced diameter portion 68d of the end member 68, with the internal and external threads 106d and 68e threadedly engaging each other. In this condition, the connecting plate 94 is clamped firmly between the flange 68b of the end member 68 and the washer 108 to fix the end member 68 with respect to the connecting plate 94. In this manner, the cylinder unit 56 is fixed with respect to the base plate 52.

When the motor 54 is driven, its output shaft 54a is reciprocally moved along the axis of the piston rod 62.

A mounting member 110 to which the output shaft 54a is coupled has a base portion 110a and an upwardly-opening socket portion 110b of a channel-shaped cross-section at it upper portion. One side wall of the socket portion 110b facing away from the motor 54 has an upwardly-opening notch 110c. A slide plate 112 of a rectangular cross-section is secured to the lower surface of the base portion 110a. An elongated guide plate 114 is secured to the upper surface of the base plate 52, and has a groove 114a formed in the upper surface thereof and extending therealong, the groove 114a extending along the axis of the piston rod 62. The slide plate 112 is fitted in the groove 114a of the guide plate 114 for sliding movement therealong. A first engaging member 116 of a channel-shaped cross-section is fitted in and secured to the socket portion 110b of the mounting member 110, the engaging member 116 having an open top. The engaging member 116 has opposed side walls and a bottom wall interconnecting the side walls at their lower ends, and has a pair of continuous grooves 116a formed in the inner surfaces of the side walls and bottom wall spaced along the axis of the piston rod 62, each of the grooves 116a being disposed in a plane perpendicular to the axis of the piston rod 62. One side wall of the engaging member 116 directed away from the motor 54 has an upwardly-opening notch 116b aligned with the notch 110c of the socket portion 110b.

A second engaging member 118 comprises a tubular body fixedly mounted on one end of the piston rod 62 remote from the end member 68. The second engaging member 118 has a pair of retaining flanges 118a formed around the tubular body and spaced along a length thereof, the flanges 118a being fitted respectively in the grooves 116a for sliding movement upwardly in a direction perpendicular to the axis of the piston rod 62, the fitting of the flanges 118a in the grooves 116a preventing the axial movement of the piston rod 62 against the mounting member 110.

With the motor 54 is driven to reciprocate the output shaft 54a, the mounting member 110 is reciprocally moved back and forth at a short stroke through the sliding engagement of the slide plate 112 with the guide member 114 so as to operate the cylinder unit 56, thereby imparting oscillation to the respiratory gas in the patient circuit 10a.

When the cylinder unit 56 is to be mounted on the base plate 52 to assembly the oscillator 50, the cylinder unit 56 is first positioned with respect to the base plate 52 in such a manner that the second engaging member 118 and the end member 68 are disposed in vertical registry with the socket portion 110b of the first engaging member 116 and the opening 94a of the connecting plate 94, respectively. Then, the cylinder unit 56 is moved downwardly toward the base plate 52, so that the flanges 118a of the second engaging member 118 are slidably fitted in the respective grooves 116a of the first engaging member 116. At the same time, the cylindrical body 68a of the end member 68 is slidably fitted in the notch 94a of the connecting plate 94. Then, the fastening member 106 is rotated to tighten the threaded engagement between the annular portion 106b and the reduced diameter portion 68d, thereby firmly clamping the connecting plate 94 between the flange 68b of the end member 68 and the washer 108 to hold the cylinder unit 56 against movement relative to the base plate 52 and the motor 52.

When the cylinder unit 56 is to be removed from the base plate 52, the fastening member 106 is first rotated to loosen the threaded engagement between the annular portion 106b and the reduced diameter portion 68d to release the clamping of the connecting member 94 between the washer 108 and the flange 68b of the end member 68. Then, the cylinder unit 56 is moved upwardly, that is, in the direction perpendicular to the axis of the piston rod 62, so that the cylindrical body 68a is moved out of the notch 94a of the connecting member 94, with the second engaging member 118 being moved upwardly out of the first engaging member 116, thereby disconnect the cylinder unit 56 from the base plate 52 and the motor 54.

What is claimed is:

1. An oscillator for imparting oscillation at a high frequency to respiratory gas in a pneumatic circuit of a high frequency oscillatory ventilation apparatus for artificial respiration, said oscillator comprising:
   (a) an elongated base plate;
   (b) a motor mounted on said base plate and having an output shaft for reciprocal movement along an axis thereof;
   (c) a cylinder unit comprising a cylinder adapted to be connected to the pneumatic circuit, a piston rod slidably extending through said cylinder along an axis thereof, and a piston fixedly mounted on said piston rod and received in said cylinder for sliding movement therealong for applying oscillation to the pneumatic circuit;
   (d) a first engaging means mounted on said output shaft of said motor;
   (e) a second engaging means mounted on said piston rod, said first engaging means engaging said second engaging means to connect said output shaft to said piston rod to reciprocally move said piston, said first engaging means engaging said second engaging means in a manner to allow said second engaging means to move out of engagement therewith in a direction perpendicular to an axis of said piston rod;
   (f) a third engaging means on said base plate, there being provided a fourth engaging means on said cylinder, said third engaging means engaging said fourth engaging means in a manner to allow said fourth engaging means to move out of engagement therewith in said direction; and
   (g) fastening means for releasably holding said fourth engaging means against movement relative to said third engaging means, thereby holding said cylinder unit against movement relative to said base plate and said motor.

2. An oscillator according to claim 1, in which said cylinder includes an end plate secured to one end thereof, said end plate having a port therethrough, and a relief valve being mounted in said port for being opened when a pressure in said cylinder chamber reaches a predetermined level to thereby communicate an interior of said cylinder with ambient atmosphere.

3. An oscillator according to claim 1, in which said first engaging means includes an engaging member of a generally channel-shaped cross-section opening in said direction and having opposed side walls and a bottom wall interconnecting said side walls at their one ends, said engaging member being connected to said output shaft and having at least one continuous groove formed in inner surfaces of said side walls and bottom wall, said groove being disposed in a plane perpendicular to the axis of said piston rod, said second engaging means comprising a tubular body mounted on one end of said piston rod and having at least one peripheral flange around said tubular body, said tubular body being received in said channel-shaped body with said flange being slidably fitted in said groove to prevent an axial movement of said piston rod, said third engaging means comprising a plate member fixedly secured to said base plate and extending perpendicular thereto, said plate member having a notch formed therethrough and opening in said direction, and said fourth engaging means comprising a cylindrical body slidably fitted in said opening.

4. An oscillator according to claim 3, in which said fastening means includes an annular portion having internal threads formed on an inner peripheral surface thereof, said cylindrical body having a second peripheral flange therearound, said cylindrical body having external threads formed on an outer peripheral surface thereof in axially spaced relation to said second flange, said cylindrical body being slidably fitted in said notch of said plate member at a portion thereof intermediate said second flange and said external threads, said annular portion threadedly engaging said cylindrical body through said internal and external threads, and said plate member being releaseably clamped between said second flange and said annular portion.

5. An oscillator according to claim 3, in which there is provided a mounting member having a socket portion of a channel-shaped cross-section opening in said direction, said channel-shaped engaging member being received in said socket portion and secured thereto, a guide plate being secured to said base plate and having a guide groove extending along the axis of said piston rod, an elongated slide plate being secured to said mounting member and being received in said guide groove for sliding movement therealong.

* * * * *